US007004969B2

(12) United States Patent
Ishikubo et al.

(10) Patent No.: US 7,004,969 B2
(45) Date of Patent: Feb. 28, 2006

(54) ARTIFICIAL SKIN AND METHOD FOR EVALUATING UV SCREENING AGENT BY USE OF THE SAME

(75) Inventors: Akira Ishikubo, Kanagawa (JP); Tohru Okamoto, Kanagawa (JP); Hideo Nakajima, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 390 days.

(21) Appl. No.: 10/320,549

(22) Filed: Dec. 17, 2002

(65) Prior Publication Data
US 2003/0109927 A1 Jun. 12, 2003

Related U.S. Application Data

(62) Division of application No. 09/859,443, filed on May 18, 2001, now abandoned.

(30) Foreign Application Priority Data

May 19, 2000 (JP) .............................. 2000-148557

(51) Int. Cl.
*A61F 2/10* (2006.01)
(52) U.S. Cl. ....................................... 623/15.12; 436/5
(58) Field of Classification Search ............. 623/15.11, 623/15.12; 602/43, 47, 52; 523/113; 424/424, 424/425; 434/267; 436/5
See application file for complete search history.

(56) References Cited

U.S. PATENT DOCUMENTS

| | | | | |
|---|---|---|---|---|
| 5,053,340 A | * | 10/1991 | Bergman et al. | 436/5 |
| 5,691,158 A | * | 11/1997 | Reece et al. | 435/7.92 |
| 5,727,567 A | * | 3/1998 | Carnaby et al. | 128/857 |
| 6,093,200 A | * | 7/2000 | Liu et al. | 606/228 |
| 6,410,333 B1 | * | 6/2002 | Rouabhia et al. | 436/63 |

* cited by examiner

*Primary Examiner*—Corrine McDermott
*Assistant Examiner*—William H Matthews
(74) *Attorney, Agent, or Firm*—Townsend & Banta

(57) ABSTRACT

Artificial skin having a thickness of 100 to 1,000 μm, and prepared from a polymer which, when formed into a thin film having a thickness of 100–1,000 μm, exhibits a percent transmission of light having a wavelength of 450–280 nm of at least 10%. In the artificial skin of the present invention, grooves which imitate furrows are provided on one surface. Also disclosed is a method for evaluating UV screening agents making use of the artificial skin of the present invention, on the basis of the relation between UV shielding power of a UV screening agent and UV transmission through the artificial skin.

1 Claim, 5 Drawing Sheets

ARTIFICIAL SKIN AND METHOD FOR EVALUATING UV SCREENING AGENT BY USE OF THE SAME

CROSS REFERENCE TO A RELATED APPLICATION

This is a divisional application of application Ser. No. 09/859,443 filed May 18, 2001 now abandoned.

BACKGROUND OF THE INVENTION

1. Field of the Invention

The present invention relates to artificial skin and to a method for evaluating UV (ultraviolet ray) screening agents by use of the artificial skin.

2. Related Art

Today, UV screening agents are incorporated into a broad range of skin external compositions, such as cosmetics. Needless to say, when a UV screening agent is incorporated into a skin external composition, the agent must first be tested so as to verify its UV shielding effects.

In such a test, if actual human skin or animal skin is used, results are surely reliable. However, from the viewpoints of safety of the test and prevention of cruelty to animals, tests using living bodies should be avoided if possible.

On the basis of the above standpoint, attempts have been made to test and evaluate UV screening agents by use of artificial skin which mimics the human skin.

For example, in one evaluation method, porous tape (TRANSPORE™ surgical tape, product of 3M Healthcare) is used as a skin substitute membrane (J. Soc. Cosmet. Chem., 40, 127–133, 1989, Diffy & Robson), and in another method, a resin-made skin replica is used as a skin substitute membrane (Int. J. Cos. Sci., 9, 85–98, 1987, Stockdale; Japanese Patent Application Laid-Open (kokai) No. 5-248944). However, the former method, which employs porous tape, is accompanied by the risk that UV screening effects might be overestimated, because the UV screening agent penetrates and is absorbed into the interior of the tape. Meanwhile, in relation to the latter case, silicone resins used as the material for making the resin-made skin replica involve a problem in terms of UV transmission, and urethane resins also used for the same purpose involve a problem in terms of sorption of the UV screening agent.

Accordingly, for evaluating UV screening agents, there is still need for an effective in vitro evaluation method making use of artificial skin having properties as similar as possible to those of real skin, with respect to UV screening agents.

SUMMARY OF THE INVENTION

Through careful studies, the present inventors have confirmed that when a UV screening agent is applied to the skin, the agent mostly remains on the skin, and the amount of transdermal absorption of the agent is so small that the UV protective or shielding effect is not affected. Accordingly, they have found that an artificial skin capable of simulating the behaviors of UV absorbents applied to real skin can be created 1) from a material which has UV-ray transmission similar to that of the epidermis and which sorbs a minimal level of UV screening agents and 2) through processing the material so as to mimic the surface of real skin. The inventors have continued their research, and have now completed the present invention.

Accordingly, the present invention provides artificial skin having a thickness of 100 to 1,000 µm, which is prepared from a polymer which, when formed into a thin film having a thickness of 100–1,000 µm, exhibits a percent transmission of light having a wavelength of 450–280 nm of at least 10%, wherein grooves which imitate furrows are provided on one surface of the artificial skin.

The present invention also provides a method for evaluating UV screening agents (hereinafter referred to as the evaluation method of the present invention) on the basis of the relation between the UV shielding power of a UV screening agent and the degree of UV transmission through the artificial skin of the present invention to which the UV screening agent has been applied on the side having furrow-imitating grooves.

BRIEF DESCRIPTION OF THE DRAWINGS

These and other objects, features and many of the attendant advantages of the present invention will be readily appreciated as the same becomes better understood by reference to the following detailed description of the preferred embodiments when considered in connection with the accompanying drawings, in which.

DESCRIPTION OF THE INVENTION AND PREFERRED EMBODIMENTS

Figure 1:
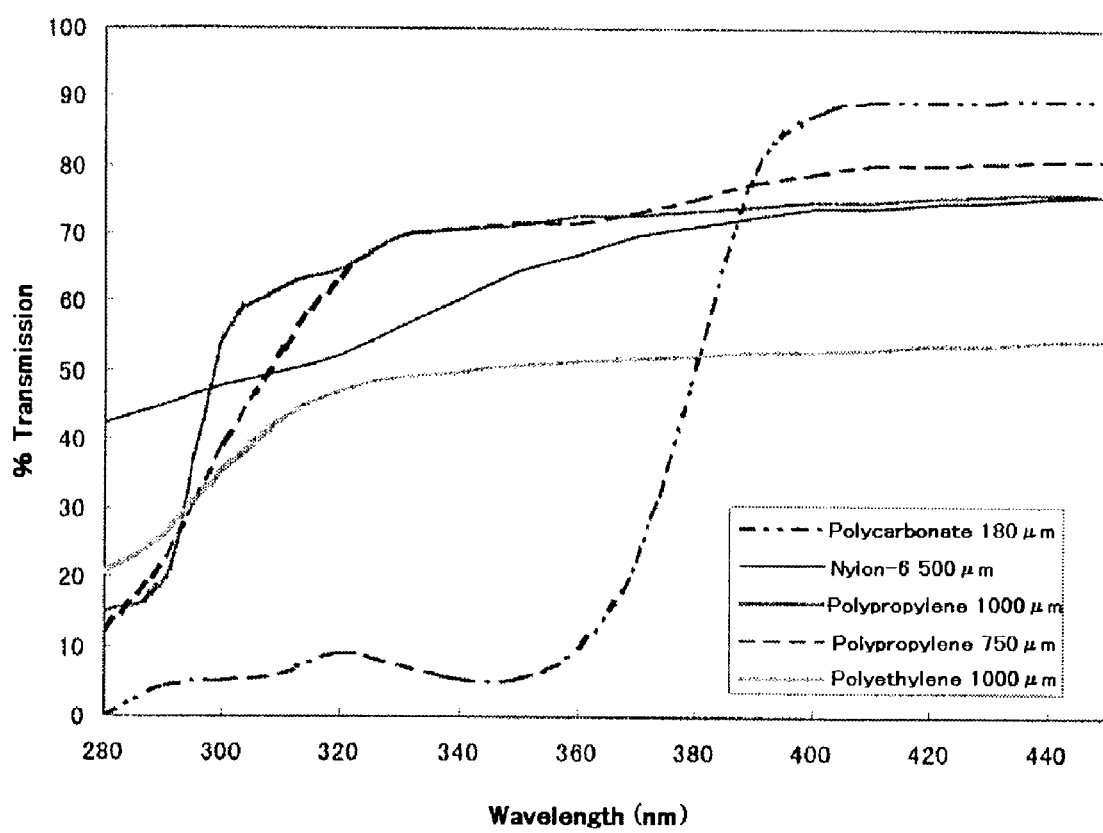
FIG. 1 shows the results of study on raw materials suitable for the artificial skin of the present invention by way of the UV transmission method.

The present invention will next be described in detail.

A. Material and Structure of the Artificial Skin of the Present Invention

The material of the artificial skin of the present invention is a polymer which, when formed into a thin film having a thickness of 100–1,000 µm, exhibits a percent transmission of light having a wavelength of 450–280 nm of at least 10%.

The reason for setting the thickness to 100–1,000 µm is that the thickness of the epidermis falls approximately within this range. If the artificial skin product had a thickness that falls outside this range, such a product would not properly serve as a skin model. The material of the artificial skin of the present invention can thus be chosen from among polymers which, when formed into a thin film having a thickness that falls within the aforementioned range, exhibit a percent transmission of light having a wavelength of 450–280 nm of at least 10%. The conditions relating to wavelength and light transmission are determined from the following a) and b). a) The wavelength range of 450–280 nm covers most medium-wavelength UV rays (UV-B) and long-wavelength UV rays (UV-A). b) The UV transmission of the epidermis with respect to UV rays having a wavelength falling within this range is about 10% or more. Example polymers that meet the above requirements include nylons in general (specific examples include nylon-6 and nylon-66), polypropylenes, and polyethylenes. Nylons are preferred, because they sorb substantially no UV screening agent and thus their use can prevent overestimation of UV shielding effect of UV screening agents.

A thin film of the aforementioned polymer having a thickness of 100–1,000 µm can be prepared from the polymer according to a conventional method or commercially available.

The artificial skin of the present invention must have furrow-imitating grooves on one surface thereof. This requirement is necessary in order to allow reproduction of the furrow structure of the epidermis. Reference to "one surface" is provided because the furrows found in the epidermis of real skin exist only on the skin surface (i.e., on only one surface).

The grooves which imitate the furrows preferably satisfy the following requirements so as to mimic the average furrow structure in actual epidermis:
1) The cross section of each groove cut along the short side has a V shape.
2) The apex angle of the V shape is 60–150°.
3) The depth of each groove is 30–100 µm.
4) The width of each groove is 50–300 µm.
5) The frequency of grooves that cross a unit length along or perpendicular to the length is 0.5–2.0 grooves/mm.
6) The frequency of grooves that obliquely cross a unit length is 0.5–2.0 grooves/mm.

The method for forming such a surface structure of the artificial skin of the present invention is not particularly limited, and cutting by use of a cutter or molding by use of a mold may be employed in order to form a desired surface structure.

In view of the structure of actual epidermis, in the artificial skin of the present invention, the areas other than the furrow-imitating groove portions in the surface preferably have micro-irregularities or a rough surface. Such micro-irregularities may be formed through, but are not limited to, chemical treatment, filing or similar means, or blasting. Blasting is preferred in that it facilitates provision of products of uniform quality in terms of micro-irregularity.

The artificial skin of the present invention can be manufactured by forming, on one surface of a thin film of the aforementioned polymer, a furrow-imitating groove structure and preferably, on the areas other than the grooved portions in the surface, micro-irregularities, so as to meet the above-described requirements.

B. Evaluation Method of the Present Invention

In the evaluation method of the present invention, UV screening agents are evaluated on the basis of the relation between the UV shielding power of a UV screening agent and the degree of UV transmission through the artificial skin of the present invention to which the UV screening agent has been applied on the side having furrow-imitating grooves. In this method, the performance or the characteristic features of the artificial skin of the present invention can be most precisely exhibited.

That is, the artificial skin of the present invention is designed so as to reflect the behaviors of UV screening agents or UV rays on actual epidermis, and thus can be properly used in the evaluation of UV screening agents.

The UV screening agents which may be used in the evaluation method of the present invention are not particularly limited, and there may be employed a broad range of UV screening agents, including those which are generally categorized as UV absorbents and those which are generally categorized as UV blockers.

Examples of UV absorbents to which the evaluation method of the present invention can be applied include p-aminobenzoic acid-based UV absorbents such as p-aminobenzoic acid, monoglyceryl p-aminobenzoate, ethyl p-N,N-dipropoxyaminobenzoate, ethyl p-N,N-diethoxyaminobenzoate, ethyl p-N,N-dimethylaminobenzoate, butyl p-N,N-dimethylaminobenzoate, and methyl p-N,N-dimethylaminobenzoate; anthranilic acid-based UV absorbents such as homomenthyl N-acetylanthranilate; salicylic acid-based UV absorbents such as amyl salicylate, menthyl salicylate, homomenthyl salicylate, octyl salicylate, phenyl salicylate, benzyl salicylate, p-isopropanolphenyl salicylate; cinnamic acid-based UV absorbents such as octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl methoxycinnamate (2-ethylhexyl 4-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl octanoate di-p-methoxycinnamate, and 3-methyl-4-[methylbis(trimethylsiloxy)silyl]butyl 3,4,5-trimethoxycinnamate; benzophenone-based UV absorbents, such as 2,4-dihydroxybenzophenone, 2,2'-dihydroxy-4-methoxybenzophenone, 2,2'-dihydroxy-4,4'-dimethoxybenzophenone, 2,2'4,4'-tetrahydroxybenzophenone, 2-hydroxy-4-methoxybenzophenone, 2-hydroxy-4-methoxy-4'-methylbenzophenone, a salt of 2-hydroxy-4-methoxybenzophenone-5-sulfonic acid, 4-phenylbenzophenone, 2-ethylhexyl-4'-phenylbenzophenone-2-carboxylate, 2-hydroxy-4-n-octoxybenzophenone, and 4-hydroxy-3-carboxybenzophenone; and other UV absorbents such as 3-(4-methylbenzylidene)-d,l-camphor, 3-benzylidene-d,l-camphor, urocanic acid, ethyl urocanate, 2-phenyl-5-methylbenzoxazole, 2-(2-hydroxy-5-t-octylphenyl)benzotriazole, 2-(2-hydroxy-5-methylphenyl)benzotriazole, dibenzalazine, dianisoylmethane, 4-t-butyl-4'-methoxydibenzoylmethane, 5-(3,3-dimethyl-2-norbornylidene)-3-pentan-2-one, and 2,4-6-tris[4-(2-ethylhexyloxycarbonyl]anilino]-1,3,5-triazine.

Examples of UV blockers to which the evaluation method of the present invention can be applied include metal oxides such as titanium dioxide and zinc oxide.

According to the evaluation method of the present invention, an essential requirement is that the degree of UV transmission of the artificial skin of the present invention (to which a UV screening agent has been applied on one surface that bears furrow-imitating grooves) be related to the UV shielding power of a UV screening agent. Thus, the first step is to measure the UV transmission through the artificial skin of the present invention to which the UV screening agent has been applied as specified above.

Typically, through detection of a transmission spectrum of UV rays having desired wavelengths that fall within the aforementioned range, percent UV transmission of UV rays of interest can be measured. Such measurement may use known means such as a spectrophotometer (preferably equipped with an integrating sphere), or a multi-photometric detector using a Xe arc solar simulator as a light source.

On the basis of the thus-obtained UV transmission spectra measured by the aforementioned measurement means, UV screening agents can be compared one another in terms of the shielding power against UV rays, or, on the basis of results of such a comparison, SPF values can be calculated (e.g., according to the SPF calculation method as disclosed in Japanese Patent Application Laid-Open (kokai) No. 7-167781) to thereby relate the UV transmission to UV shielding power.

The evaluation method of the present invention enables proper evaluation of the UV shielding effect of UV screening agents without use of actual epidermis, to thereby significantly reduce the number of tests to be performed on humans or animals.

EXAMPLES

The present invention will next be described in detail by way of examples, which should not be construed as limiting the invention thereto. In the Examples hereunder, unless otherwise specified, amounts of the substances are expressed in mass percent (mass %) with respect to the composition to which the substances are added.

A. Study on Materials for Preparing the Artificial Skin

A preliminary test was carried out in order to select suitable raw materials for preparing the artificial skin of the present invention (hereinafter the raw materials are also referred to simply as the artificial skin materials).

Study on Materials on the Basis of Transmission

Within the UV range, the percent transmission of the following thin films was obtained so as to determine, for the artificial skin material of the present invention, materials that satisfy the requirement of having "a percent transmission of light having a wavelength of 450–280 nm of at least 10%, when formed into a thin film having a thickness of 100–1,000 $\mu$m."

| | |
|---|---|
| 1) Polycarbonate | (thickness: 180 $\mu$m) |
| 2) Nylon-6 | (thickness: 500 $\mu$m) |
| 3) Polypropylene | (thickness: 1,000 $\mu$m, 750 $\mu$m) |
| 4) Polyethylene | (thickness: 1,000 $\mu$m) |

In the measurement of percent transmission of UV rays, a spectrophotometer equipped with an integrating sphere (U3410, a product of Hitachi) was employed.

FIG. 1 shows the results of the test [in the graph, x-axis: wavelength (nm) of irradiated light, y-axis: percent transmission (%)].

As shown in FIG. 1, nylon-6 and polypropylene satisfy the above requirement of having "a percent transmission of light having a wavelength of 450–280 nm of at least 10%, when formed into a thin film having a thickness of 100–1,000 $\mu$m" and thus are preferred as the artificial skin material of the present invention from the viewpoint of UV transmission.

Study on Materials on the Basis of Sorption

In addition to UV transmission, sorption of UV screening agents also serves as a criterion for the artificial skin material of the present invention. Skin sorbs substantially no UV screening agents, and therefore materials having such sorption property are preferably selected for the artificial skin material of the present invention. In addition, when a UV screening agent is sorbed into artificial skin, there is a stronger tendency to overestimate the UV shielding effect of the UV screening agent.

A test was carried out in the following manner. A UV screening agent solution containing octyl methoxycinnamate (UV screening agent), decamethylcyclopentasiloxane (liquid silicone oil), and pentaerythritol tetra-2-ethylhexanoate (ester oil), at proportions by mass of 20:30:30, was prepared. Thin film samples (thickness: each 500 $\mu$m) of nylon-6 and polypropylene were immersed in the solution for a period of half a day. Subsequently, the samples were removed from the solution, and washed thoroughly with ethanol. Before and after the UV screening agent treatment, UV transmission was measured for each sample of the thin polymer films by use of the above-described spectrophotometer equipped with an integrating sphere.

Figure 2:
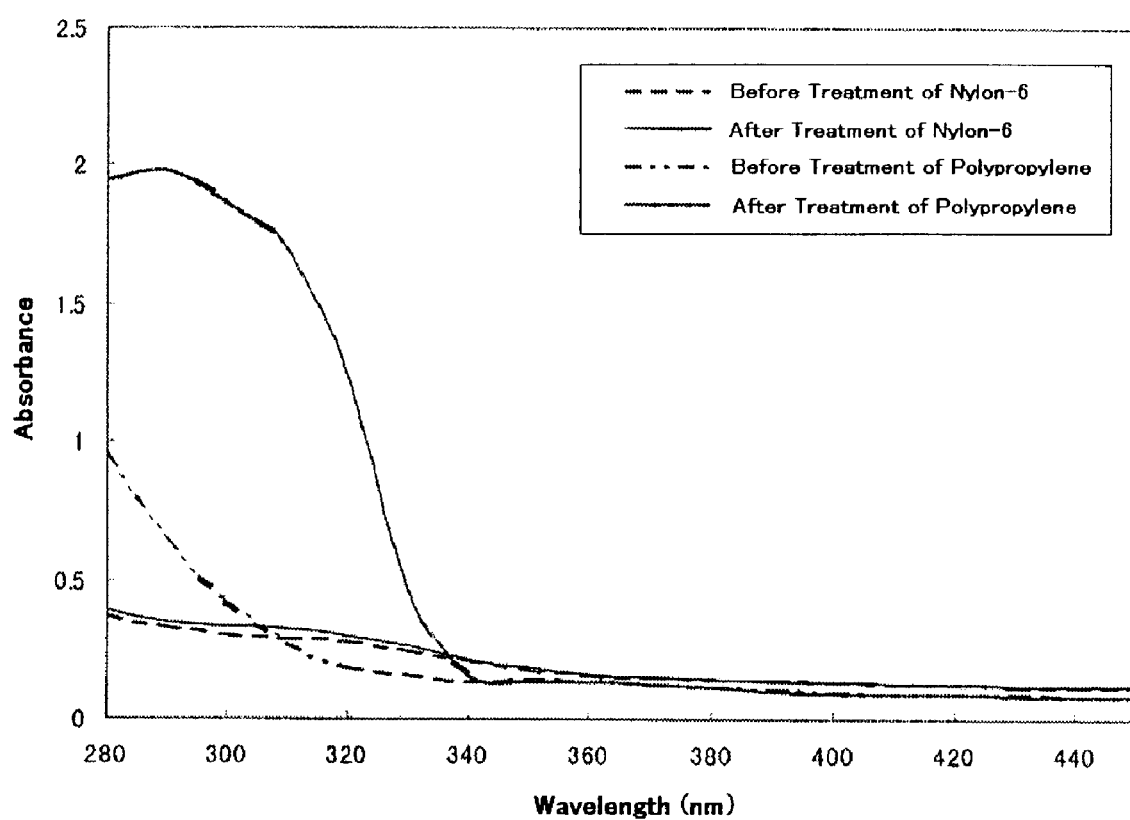
FIG. 2 shows the results of study on raw materials suitable for the artificial skin of the present invention with respect to sorption of UV screening agents.

FIG. 2 shows the results of the above test (x-axis: wavelength (nm) of irradiated light, y-axis: absorbance) As shown in FIG. 2, the absorbance of the polypropylene, particularly within the UV-B range, varied before and after the above treatment (i.e., the absorbance after the treatment increased). This clearly indicates that, as a result of the above immersion treatment, octyl methoxycinnamate, a UV-B absorbent, was sorbed and remained on the film of the polypropylene. In contrast, the nylon-6 film shows no difference in absorbance before and after the treatment over the entirety of the measured range. This shows that octyl methoxycinnamate was not substantially sorbed into the nylon-6 film.

The results of the above test show that nylons, in particular nylon-6, are preferred as material of the artificial skin of the present invention.

B. Production of the Artificial Skin

In accordance with the results of the above test, nylon-6 (thin film (thickness: 500 $\mu$m)) was employed as the material for the artificial skin of the present invention. On one surface of the thin film, groove structure satisfying the below-described conditions (1) to (7) was provided through cutting by use of a cutter, and furthermore micro-irregularities are provided on the areas other than the groove portions in the surface through blast treatment (treatment of beating with small glass beads at high speed) to form a rough surface, in consideration of the configuration of the surface of human skin having furrows (depth of furrow: 50–100 $\mu$m, width of furrow: about 100 $\mu$m, number of furrows: 1–2 furrows/mm) and the fact that the furrows expand when a skin external composition is applied to.

(1) The cross section of each groove cut along the short side has a V shape.
(2) The apex angle of the V shape is 105°.
(3) The depth of each groove is 76 $\mu$m.
(4) The width of each groove is 200 $\mu$m.
(5) The frequency of grooves that cross a unit length along the length is 1 groove/mm.
(6) The frequency of grooves that cross a unit length perpendicular to the length is 0.5 groove/mm.
(7) The frequency of grooves that obliquely cross a unit length is 0.5 grooves/mm.

Figure 3A:
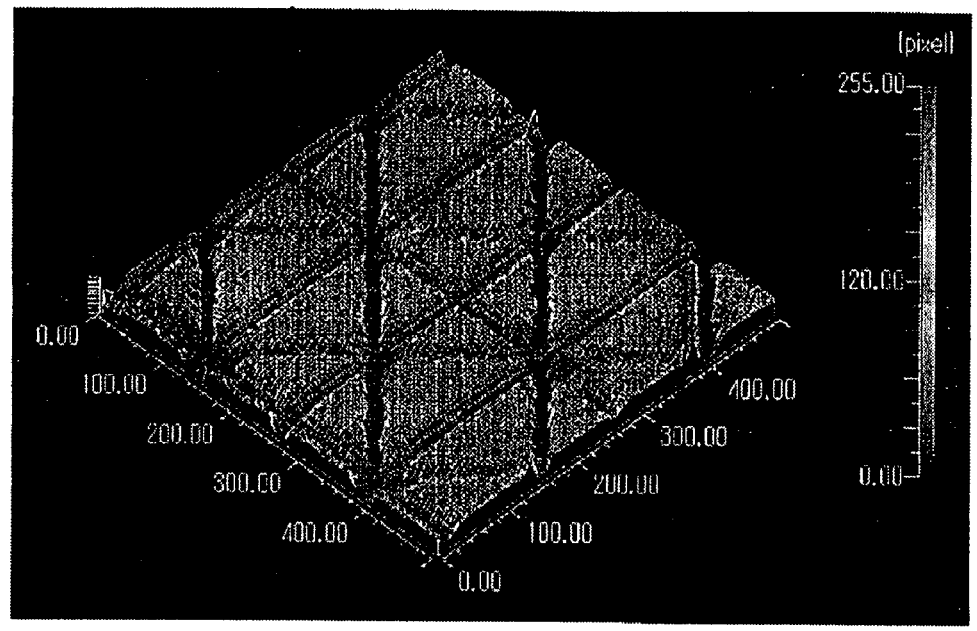
FIGS. 3A and 3B show the surface configurations of the artificial skin of the present invention and a representative comparative product.
Figure 3B:
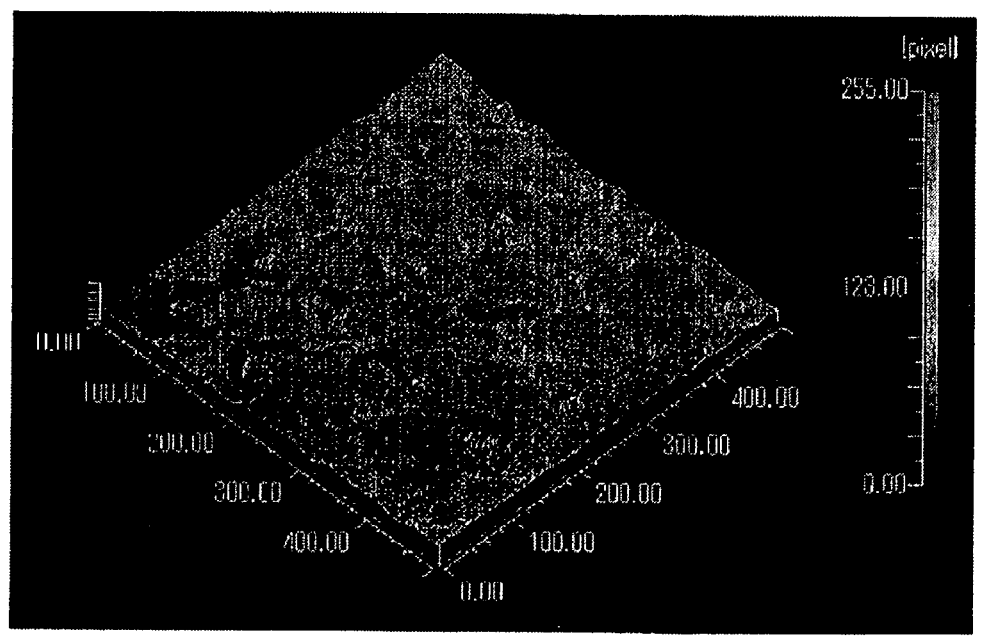

FIG. 3A shows the surface configuration of the artificial skin of the present invention having the above-described structure, and FIG. 3B shows the surface configuration of a commercially available porous tape (TRANSPORE™ surgical tape, product of 3M Healthcare) for comparison. As shown in FIG. 3A, the surface configuration of the artificial skin of the present invention is similar to that of human skin. In contrast, the surface configuration of the porous tape shown in FIG. 3B is less similar to that of human skin, posing expected problems relating to the reproduction, or simulation, of the behavior of UV screening agents on real skin. Moreover, leaching out, through pores in the porous tape, of test agents containing a UV screening agent, and permeation of UV screening agents into an adhesive layer are also expected, and these factors altogether contribute to problems related to the aforementioned reproduction.

C. The Evaluation Method of the Present Invention

The artificial skin of the present invention in FIG. 3A and a porous tape shown in FIG. 3B (TRANSPORE™ surgical tape, product of 3M Healthcare, serving as a product for comparison) were compared for assessment of the utility of the evaluation method according to the invention. W/O sunscreens of the below-described compositions (Table 1, A–F) were employed as the samples for the study of UV shielding effect.

TABLE 1

|  | A | B | C | D | E | F |
|---|---|---|---|---|---|---|
| Octyl methoxycinnamate | 7.5 |  | 5 | 5 | 7.5 |  |
| 2-Hydroxy-4-methoxy-benzophenone | 0.6 |  |  |  |  |  |
| 4-tert-Butyl-4'-methoxybenzoylmethane |  |  |  |  | 2 |  |
| 2,4,6-tris[4-(2-Ethylhexyloxycarbonyl)-anilino]-1,3,5-triazine |  |  |  | 1 |  |  |
| TiO$_2$ |  | 7 | 3 | 5 |  | 6 |
| ZnO |  |  |  |  |  | 10 |
| Purified Water | 38.5 | 38.5 | 38.5 | 38.5 | 38.5 | 38.5 |
| 1,3-Butylene glycol | 5.0 | 5.0 | 5.0 | 5.0 | 5.0 | 5.0 |
| Squalane | 52.0 | 52.0 | 52.0 | 52.0 | 52.0 | 52.0 |
| Glyceryl diisostearate | 3.0 | 3.0 | 3.0 | 3.0 | 3.0 | 3.0 |
| Organophylic montmorillonite | 1.5 | 1.5 | 1.5 | 1.5 | 1.5 | 1.5 |
| Preservative | q.s. | q.s. | q.s. | q.s. | q.s. | q.s. |
| Perfume | q.s. | q.s. | q.s. | q.s. | q.s. | q.s. |
| SPF | 8 | 16 | 18 | 25 | 30 | 30 |

In a manner similar to that described for the above section A in Examples, the artificial skin serving as a test subject was coated on its rough surface with one of the above sunscreens A–F in an amount of 2 mg/cm$^2$, and subjected to analysis of UV transmission spectrum. The measurements were converted into in vitro SPF values according to the known SPF calculation method (Japanese Patent Application Laid-Open (kokai) No. 7-167781, Example 1 (described in paragraph Nos. 0024 to 0037)).

The results and the in vivo SPF values—measured by a test institute on the basis of the general method for determining SPF values employing humans (see the bottom line in Table 1)—were compared to thereby study the utility of the evaluation method of the present invention.

Figure 4:
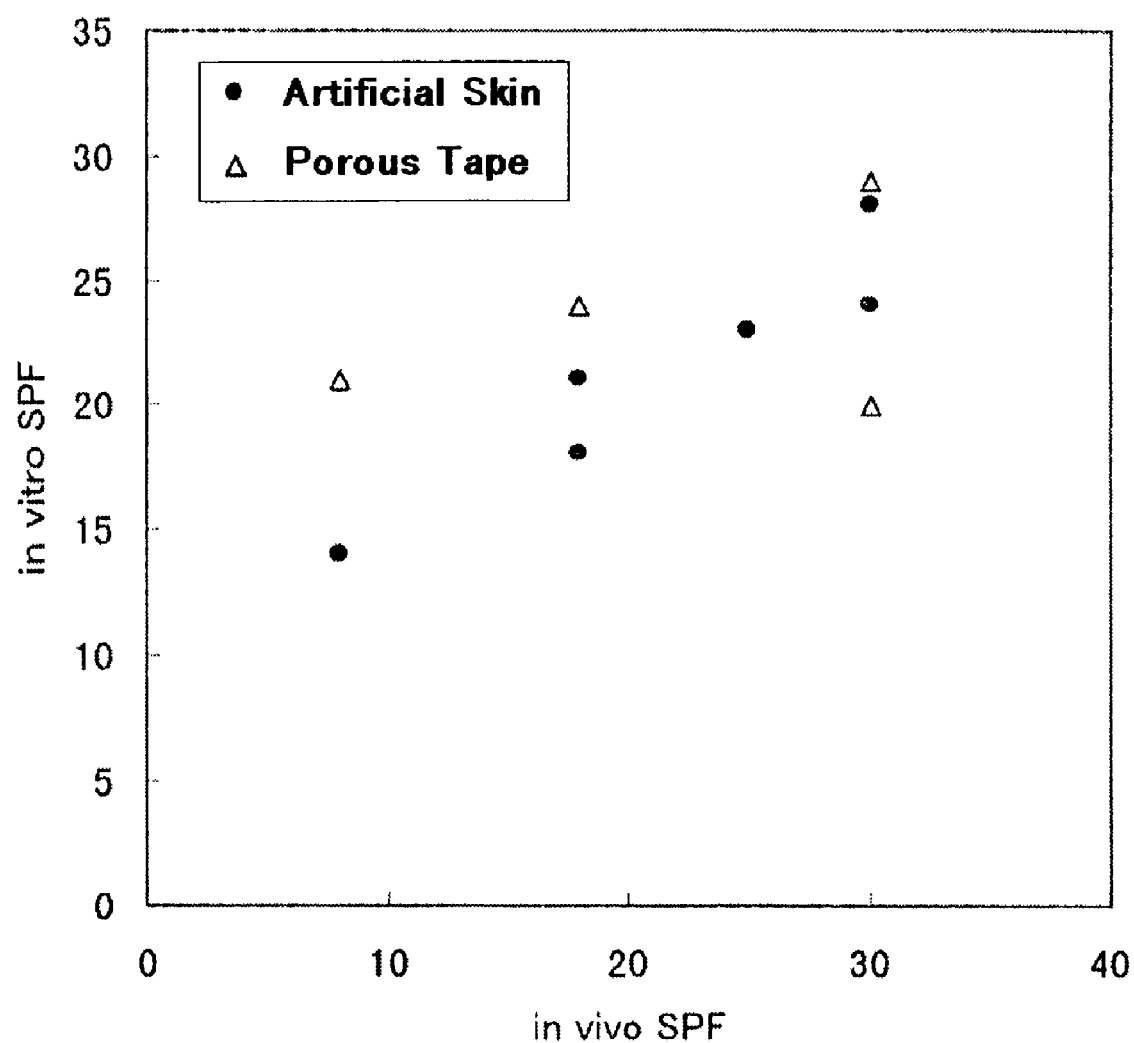
FIG. 4 shows correlation between SPF values calculated from the results of the in vivo test and those calculated from the results of the test using the artificial skin of the present invention.

FIG. 4 shows the results of the above comparison (x-axis: SPF values calculated by the general method, y-axis: SPF values calculated by the evaluation method of the present invention.)

When the artificial skin was used, y-axis SPF values and x-axis SPF values were almost correlative; therefore, the evaluation method employing the artificial skin of the present invention was proven to be highly reliable. In contrast, when porous tape was used, the results varied broadly; therefore, it was proven that it was difficult to obtain reliable data when the tape was used.

(2) Study Over Time on Shielding Effect, Against UV Rays, of Artificial Skin Coated with a Sunscreen While the wavelengths of UV rays were fixed to fall within the range of UV-B, UV absorbance of the artificial skin coated with a sunscreen was measured over time, and thus, actual effects exerted by the sorption of the sunscreen were investigated.

The below-described W/O-emulsified sunscreen was prepared as a sample to be tested for shielding effects against UV rays.

| Ingredient | Amount (mass %) |
|---|---|
| (Ingredient A) | |
| octyl methoxycinnamate | 2.0 |
| decamethylcyclopentasiloxane | 30.5 |
| trimethylsiloxysilicate | 2.5 |
| dimethylpolysiloxane | 5.0 |
| POE methylpolysiloxane copolymer | 1.0 |
| dimethyldistearylammonium hectorite | 0.7 |
| (Ingredient B) | |
| 1,3-butanediol | 5.0 |
| purified water | balance |

<Preparation Method>

The ingredients A were stirred with a homomixer, and the ingredients B were gradually added thereto with stirring, to thereby prepare a W/O sunscreen.

The sunscreen was applied to each of the test samples (the artificial skin in FIG. 3A and the porous tape in FIG. 3B). The sunscreen was applied to the rough surface of the samples in an amount of 2 mg/cm$^2$. The absorbance was measured at 310 nm over time according to the method described in the above section A in Examples.

Figure 5:
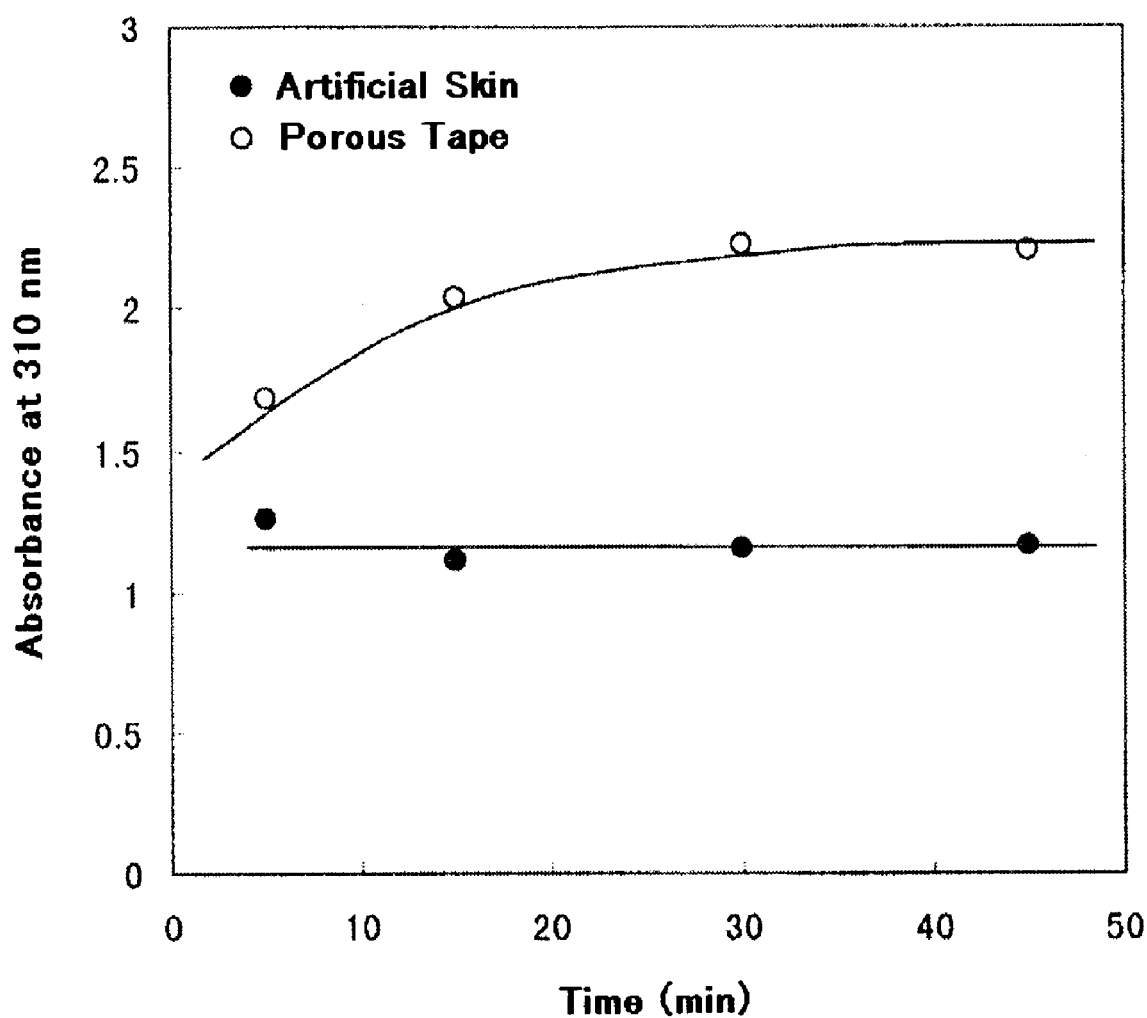
FIG. 5 shows the results of study on the UV shielding effect over time with respect to application of a sun screen agent on the artificial skin.

FIG. 5 shows the results of the above test (in the graph, x-axis: time lapsed after application, y-axis: absorbance at 310 nm).

As shown in FIG. 5, the UV shielding effect of the sunscreen on the artificial skin of the present invention was stable. In contrast, the UV shielding effect of the sunscreen on the porous tape increased over time. In view that the sunscreen or the UV screening agent per se cannot increase the UV shielding effect over time, the increase in the UV shielding effect as observed in the case of porous tape is considered to be attributed to sorption of the sunscreen or the UV screening agent into the tape surface. Thus, the UV shielding effect of the sunscreen or the UV screening agent on the porous tape is overestimated, and therefore use of the porous tape in an in vitro UV shielding effect test involves a high risk. In the case of the artificial skin of the present invention, substantially no sorption of the sunscreen or the UV screening agent was observed, and thus the artificial skin of the present invention is particularly preferable for use in an in vitro test for verifying the UV shielding effect of a sunscreen or a UV screening agent. Thus, the evaluation method of the present invention is clearly useful.

Obviously, numerous modifications and variations of the present invention are possible in light of the above teachings. It is therefore to be understood that within the scope of the appended claims, the present invention may be practiced otherwise than as specifically described herein.

What is claimed is:

1. A method for evaluating a UV screening agent, which comprises preparing artificial skin, said artificial skin having a thickness of 100 to 1,000 μm, which is prepared from a polymer which, when formed into a thin film having a thickness of 100–1,000 μm, exhibits a percent transmission of light having a wavelength of 450–280 nm of at least 10%, wherein grooves which imitate furrows are provided on one surface of the artificial skin, coating the artificial skin with the UV screening agent on the side having furrow-imitating grooves, and evaluating the UV screening agent on the basis of the relation between UV shielding power of the UV screening agent and UV transmission through the artificial skin.

* * * * *